United States Patent
Romani

[11] 3,934,577
[45] Jan. 27, 1976

[54] FETAL HEART RATE MONITORING APPARATUS

[75] Inventor: Edward Paul Romani, Holland, Pa.

[73] Assignee: Hoffmann-La Roche Inc., Nutley, N.J.

[22] Filed: Aug. 9, 1974

[21] Appl. No.: 496,247

Related U.S. Application Data

[63] Continuation of Ser. No. 313,373, Dec. 8, 1972, abandoned.

[52] U.S. Cl. .......... 128/2.05 T; 73/68.7; 128/2.05 Z
[51] Int. Cl.² ............................................. A61B 5/02
[58] Field of Search...... 128/2.05 P, 2.05 R, 2.05 T, 128/2.05 Z, 2.06 A, 2.06 F, 2.06 R; 73/67.5, 67.6, 67.7, 67.8

[56] References Cited
UNITED STATES PATENTS

| | | | |
|---|---|---|---|
| 3,554,188 | 1/1971 | Lasch et al. | 128/2.06 F |
| 3,605,723 | 9/1971 | King et al. | 128/2.05 Z |
| 3,763,851 | 10/1973 | Haff et al. | 128/2.05 T |

*Primary Examiner*—William E. Kamm
*Attorney, Agent, or Firm*—Samuel L. Welt; Bernard S. Leon; Mark L. Hopkins

[57] ABSTRACT

Ultrasonic apparatus for monitoring heartbeat activity from electrical Doppler signals derived from heartbeat motion comprising means for selective passing of the electrical Doppler signals at one of two operable bandpass ranges to a retunable resonant circuit which de-emphasizes non-resonant frequency content, means for detecting a phase shift between the input signals to and output signals from the resonant circuit to retune it at a preselected rate, and means for inhibiting the phase detector operation with one of two operable refractory periods to prevent artifact from showing as a phase shift, whereby the operable bandpass ranges and refractory period are in response to separate preselected recorded heart rate values.

5 Claims, 2 Drawing Figures

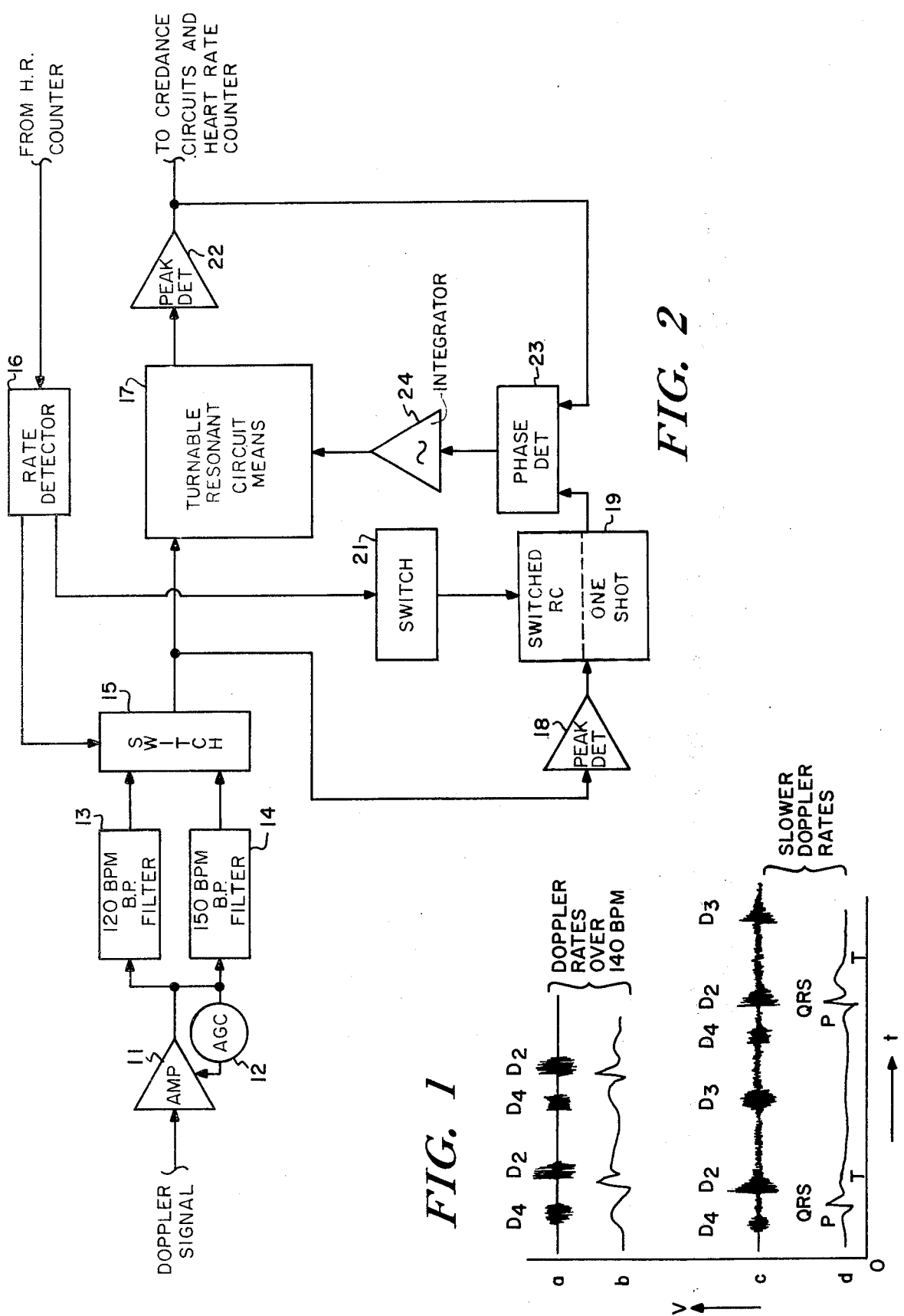

FETAL HEART RATE MONITORING APPARATUS

This is a continuation, of application Ser. No. 313,373 filed Dec. 8, 1972 and now abandoned.

BACKGROUND OF THE INVENTION

The present invention relates generally to electrical signal processing techniques utilized with an ultrasonic exploratory system and, more particularly, to signal analyzing in fetal monitoring.

In ultrasonic exploratory scanning, physiological data is derived from a patient, for monitoring and/or therapeutic purposes, by transmitting ultrasonic energy into the patient's body and then collecting and processing the data derived, in the form of an intelligence, for diagnostic purposes. However, problems are often encountered in analyzing such data due to the signals derived from the multiple sounds and associated noise collected from the body site being investigated.

In particular, in the field of fetal monitoring, the frequent movement of the fetus adds to the problem of deriving reliable signals indicative of fetal heart rate. The problem is intensified even more as a consequence of the multiple sounds generated by the front and rear wall of the heart, heart valves, etc., in addition to the nonsynchronous impulse noise caused by the fetal and mother movements. Naturally, processing of multiple signals with background noise within a single heartbeat, if processed as consecutive heartbeat signals, would produce a false indication of the fetal heart rate, and therefore provide unreliable instrumentation. Long term averaging techniques are not permissable since it is important that rapid changes in fetal heart rate be observed.

One improvement made to help obviate such problems is disclosed in U.S. Pat. Application Ser. No. 205,942, now U.S. Pat. No. 3,763,851 filed Dec. 8, 1971 by Haff and Hatke for a Fetal Monitoring Technique. The latter improvement discloses ultrasonic apparatus for monitoring heartbeat activity from Doppler shifted information derived from heartbeat motion. The Doppler shifted information is fed to an adjustable resonant circuit for de-emphasizing Doppler signal frequency content other than that about the resonant circuit frequency, and comparing input signals to, and output signals from the resonant circuit for detecing a phase difference, if any, which is employed for adjusting the frequency of the resonant circuit at a preselected rate. Such a technique provides a phase locked tracking filter which helps to suppress and eliminate undesired signals.

Despite the achievement of displaying reliable fetal heart rates with the technique disclosed in the above-referenced application, it was found that a still more reliable fetal heart rate count from the Doppler signal could be attained to provide an automatic operating system to handle the quick transition from tachycardia to bradycardia conditions which is highly desirable for monitoring fetal heart rates.

SUMMARY OF THE INVENTION

Accordingly, it is the purpose of the present invention to derive an improved beat-to-beat fetal heart rate signal by further suppression and/or elimination of signals indicative of other motions within the body and nonsynchronous impulse noise. The latter is accomplished by the provision of processing circuitry which includes variable bandpass filter switching in combination with a variable period blanking circuit switching, each of which is separately controlled to be switched into its respective operation in response to preselected fetal heart rate values sensed by a heart rate detector.

The above system is integrated with the resonant circuit technique made reference to above to further enhance its operation to provide an overall system for improved fetal heart rate accuracy. Peak detection circuitry has also been incorporated in the above system to further enhance its sensitivity.

DESCRIPTION OF THE DRAWINGS

FIG. 1 is a voltage versus time waveform diagram to show components of Doppler detected fetal heart motion in relation to EKG fast and slow cardiac activity.

FIG. 2 is a block diagram of a heart rate processing system according to the present invention.

PREFERRED EMBODIMENT OF THE INVENTION

As a consequence of extensive clinical investigation of simultaneous Doppler and fetal scalp EKG recordings, the meaning and behaviour of the detail in the Doppler signal have resulted in an analysis which was revealed distinctions in the Doppler signal make-up at different frequency ranges. At the fetal heart rate over about 140 BPM it was found that there are typically two Doppler components, one clearly related to the P-wave, probably representing atrial contraction, and a second occurring immediately after the QRS, probably representing mitral valve closure. By analogy with an electrocardiogram in FIG. 1 these are respectively labeled D-4 and D-2. Preliminary investigation shows their relation in time is constant at all heart rates. These are substantially large amplitude signals which is not surprising since the mitral and tricuspid valves are the largest and fastest moving objects within the physiological make-up.

At slower heart rates or those below about 130 another Doppler component becomes evident in diastole, specifically that designated as D3. This event is probably related to mitral or tricuspid opening. It would appear that D3 merges with D4 at higher fetal heart rates, but as the rate slows it appears to move away from D4 toward D2. This sound appears not to be constant, but when it occurs it is troublesome to counting circuits.

As will become evident, applicant after extensive evaluation and testing has devised an improved detection system for derving an improved beat-to-beat fetal heart rate by diminishing the effect of Doppler components D3 and D4 as well as other undesired noise by automatic switching circuitry which responds to preselected heart rate values to effect changes in bandpass filtering and tuning of blanking circuitry to implement operation of the resonant circuit to act as a tracking filter following the basic harmonic of the Doppler signals.

In turning to FIG. 2, the derived raw ultrasonic Doppler signal is fed to an amplifier 11 and thence through an AGC feedback unit 12 which together serves to rectify, integrate and normalize the incoming signal to form a smooth envelope of the signal. The processed signal is fed to each of a pair of bandpass filters 13 and 14 respectively having upper ends of around 120 BPM and 150 BPM, at a rolloff of 24 db/octave and each having a lower end of around 30 BPM at a rolloff of 18db/octave.

A switching unit 15 comprised, for example, of a field effect transistor pair, selectively connects one of the filters 13, 14, to an adjustable resonant circuit 17 and a peak detector 18. The switching operation is controlled by a conventional rate detector 16 which is connected from the heart rate counter. In the present embodiment the rate detector 16 is designed to respond to rates of the heart rate counter above a preselected value (e.g. 100 BPM) to operate switch 15 for passing signals emitted from the 150 BPM filter, whereas the rate detector responds at rates below the preselected value to operate switch 15 for signals emitted from the 120 BPM filter.

The resonant circuit 17, as disclosed in the above-referenced application has a resistance R, capacitance C and variable inductance L, which acts as a narrow band filter locking on to the fundamental frequency of the input. The resonant circuit, for example, in the present embodiment is electronically tuned from 5Hz to 4Hz (equivalent to 30 BPM to 240 BPM).

Positive peaks of the signal passed trigger the peak detector 18 which in turn triggers a unit 19. 19 is designed to operate at one of two RC values as determined by switch 21 to generate one of two output refractory pulse periods. Switch 21 is responsive to the output of rate detector 16 which responds to a preselected value of the heart rate counter to effect a change of the RC value of one shot 19. In the present embodiment, a one shot refractory period of 100 ms is generated when the fetal heart rate is above 140 BPM and a one shot refractory period of 350 ms is generated when the fetal heart rate is below 140 BPM. It is noted that switch 21 responds to a higher value on the heart rate counter than that responded to by switch 15.

The output of resonant circuit 17 is also connected to a peak-detector 22 whereby the resonant circuit output peak detected signal, after having been treated by peak detector 18, is fed back to be compared with the input signal to the resonant circuit via a phase detector 23 to provide a phase shift output change, if any, which is integrated by an integrator 24 for retuning the resonant circuit 17 by way of its inductance L. The output of peak detector 22 is also fed to the heart rate counter via other selected circuitry (not particularly shown) such as, for example, a credence checking circuit.

OPERATION

Assuming the fetal heart rate of a fetus being monitored is above 100 BPM switch 15 would have been acted on by rate detector 16 to open bandpass filter 14 to increase the bandpass monitoring range for the reason that as the fetal heart rate increases above 100 BPM less noise is present in the Doppler derived signal as explained above. The resonant circuit 17 to which the signals are passed acts as a narrow band filter locking on to the fundamental frequency or basic harmonic of the Doppler signals to de-emphasize noise and associated higher harmonic signals occurring at the higher end of the resonant circuit bandpass characteristic.

The resonant circuit 17 thus responds strongly to its input signal in terms of voltage amplitude at one desired frequency and discriminates against other frequencies, whereby the desired or tuned frequency is that which the resonant circuit is adjusted to, over for example, 3 to 10 seconds (the slew rate of the resonant circuit) which is the time it might take for the resonant circuit to be retuned from 0.5 to 4Hz. Should the resonant circuit be tuned to the precise frequency at the input signal, the phase shift through the circuit at phase detector 23 will be zero. If the frequency of the tuned resonant circuit is either above or below the incoming frequency, the phase shift sensed by the phase detector 23 is used as an error correcting signal via integrator 24 to retune the resonant circuit 17 to be precisely in tune with the incoming signal.

The output of the integrator acts as the control voltage which determines the slew rate of the resonant circuit. The slew rate is made to be above the lowest period of the resonant circuit, which in the present embodiment is, for example, 2 seconds or ½ cycle per second. Clearly the slew rate should not exceed a value that would not closely follow or track the actual incoming cardiac activity to which the filter is responding. The resonant circuit is then, in effect, force to track (as modified by the slew rate) the incoming signal, whereby it will not respond to impulse artifact of even 2, 3 or 4 motions per fetal cardiac cycle unless these motions are precisely harmonically related. The operation of the resonant circuit was found to be enhanced by utilizing peak detectors 22 and 18 providing the trigger signals to be supplied to phase detector 23 for the reason that peak detection allows for better signal detection in the presence of noise and eliminates base line wandering problems.

Upon the change of the output of the state of the peak detector 18 by detection of the peak input signal one-shot 19 is triggered. The one-shot provides a refractory period which serves as a blanking to inhibit operation of the phase detector in response to unwanted noise defining that period which might include attenuated portions of signals D3 and D4 (illustrated in FIG. 1). Accordingly, the window blanking prevents retuning of the resonant circuit 17 by such signals. The blanking window for optimum operation is varied to be of a shorter duration at higher frequencies and of a longer duration at lower frequencies, for example as discussed with regard to FIG. 1. Further, at the higher BPM rate a shorter blanking period suffices to override D4 whereby at lower BPM a longer period is necessary to override D3 and D4.

To enable the resonant circuit to properly respond to an increase/decrease in the derived Doppler fundamental, switching of the blanking window refractory periods and filters 13 and 14, should not occur simultaneously. The best results were obtained when assuming a 100 BPM as criteria for the filter switching, the one shot refractory period switching would occur at a heart rate meter reading of roughly 140 BPM as detected by rate detector 16.

As may be seen, the switching of the filters and the blanking window refractory periods, provide a concerted action whereby the filters and resonant circuit combine to deter a quick jump from the previously recorded heartbeat rate and whereby the blanking window refractory periods serve to improve the reliability of reading low heart rates. This, in essence, enables us to handle both tachycardia and bradycardia events with optimum reliability.

It should be understood, of course, that although only two bandpass filters and two one-shot refractory periods are disclosed, three or more of each might be employed as well as any combination or permutation of the two (e.g. three bandpass ranges anywhere from about 30 BPM to 240 BPM and 4 one-shot refractory periods.

I claim:

1. In apparatus for monitoring heart beat activity in which means are provided for obtaining electrical Doppler signals from ultrasonic Doppler shifted information derived from heartbeat motion, the arrangement comprising:
    filter means for passing a first band of frequencies including selectively actuable means for passing a second band of frequencies in lieu of the first band, of said electrical Doppler signals;
    tunable resonant circuit means for de-emphasizing in the passed band of frequencies, frequency content other than that closely about the resonant circuit frequency for providing an output signal indicative of fetal heart rate;
    phase detector means responsive to a phase shift between input signals to and output signals from the resonant circuit means, for tuning the resonant circuit means at a preselected rate in accordance with the detected phase shift;
    timing means defining a first pulse period in response to said input signals and defining a second pulse period in lieu of the first, for inhibiting the response of said phase detector means during the pulse period defined; and
    rate detector means operatively coupled to the output signal indicative of fetal heart rate for separately controlling said filter means and said timing means in response to respective preselected different values of the heart rate signal.

2. Apparatus according to claim 1 including:
    first peak detector means for providing input signals to be supplied to said timing means; and
    second peak detector means for deriving said output signals from the resonant circuit means.

3. Apparatus according to claim 1 wherein said rate detector means includes:
    a first switch means responsive to a detection of a first preselected heart rate value for actuating said filter means to pass said second band of frequencies, and
    second switch means responsive to a detection of a second preselected heart rate value for actuating said timing means to define said second pulse period for inhibiting the response of said phase detector means.

4. Apparatus according to claim 3 wherein said first preselected value is smaller in terms of beats per minute than said second preselected value.

5. Apparatus according to claim 1 wherein said rate detector means includes means responsive to a preselected value of anywhere from 85 to 115 beats per minute for actuating said filter means and responsive to a preselected value of anywhere from 125 to 155 beats per minute for actuating said timing means.

* * * * *